US009956267B2

(12) United States Patent
Vesely

(10) Patent No.: US 9,956,267 B2
(45) Date of Patent: May 1, 2018

(54) METHOD OF TREATING SKELETAL DYSPLASIAS USING VESSEL DILATOR

(71) Applicant: David Lynn Vesely, Tampa, FL (US)

(72) Inventor: David Lynn Vesely, Tampa, FL (US)

(73) Assignees: University of South Florida, Tampa, FL (US); United States Department of Veterans Affairs, Washington, DC (US)

( * ) Notice: Subject to any disclaimer, the term of this patent is extended or adjusted under 35 U.S.C. 154(b) by 33 days.

(21) Appl. No.: 14/757,770

(22) Filed: Dec. 23, 2015

(65) Prior Publication Data

US 2016/0151460 A1    Jun. 2, 2016

Related U.S. Application Data

(63) Continuation of application No. 13/693,372, filed on Dec. 4, 2012, now abandoned, which is a continuation of application No. PCT/US2011/039277, filed on Jun. 6, 2011.

(60) Provisional application No. 61/351,534, filed on Jun. 4, 2010.

(51) Int. Cl.
| | |
|---|---|
| *A61K 38/22* | (2006.01) |
| *C07K 14/58* | (2006.01) |
| *A61P 19/08* | (2006.01) |
| *A61P 19/10* | (2006.01) |
| *A61K 38/00* | (2006.01) |

(52) U.S. Cl.
CPC .......... *A61K 38/2242* (2013.01); *A61K 38/22* (2013.01); *C07K 14/58* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,599,792 A | 2/1997 | Kronis et al. | |
| 6,352,973 B1 | 3/2002 | Tam | |
| 6,743,425 B2 | 6/2004 | Nakao | |
| 7,276,481 B2* | 10/2007 | Golembo | A61K 38/2242 435/1.1 |
| 2003/0119791 A1 | 6/2003 | Kerwin et al. | |
| 2004/0127563 A1 | 7/2004 | Deslauriers | |
| 2005/0272650 A1* | 12/2005 | Mohapatra | A61K 38/2242 514/12.2 |
| 2006/0293232 A1 | 12/2006 | Levy et al. | |
| 2010/0204109 A1 | 8/2010 | Bevec | |

OTHER PUBLICATIONS

Ackerman, et al., Disposition of vessel dilator and long-acting natriuretic peptide in healthy humans after a one-hour infusion, J. Pharmacol. Exp. Therap., 1997, vol. 282 (Issue 2):603-608.
Bocciardi et al., Overexpression of the C-type natriuretic peptide (CNP) is associated with overgrowth and bone anomalies in an individual with balanced t(2;7) translocation. Hum Mut. 2007 vol. 28 (Issue 7):724-731.
Brenner et al., Diverse biological action of atrial natriuretic peptide. Physiol Rev. 1990. vol. 70:665-699.
Chusho et al., Dwarfism and early death in mice lacking C-type natriuretic peptide. Proc Natl Acad Sci. 2001. vol. 98 (No. 7):4016-4021.
Cory et al., Use of Aqueous soluble tetrazolium/formazan assay for growth assays in culture. Cancer Commun. 1991. vol. 3 (Issue 7):207-212.
Daggubati et al., Adrenomedullin, endothelin, neuropeptide Y, atrial, brain, and C-natriuretic prohormone peptides compared as early heart failure indicators. Cardiovascular Res. 1997. vol. 36:246-255.
Gough et al., Generalised bone loss in patients with early rheumatoid arthritis, The Lancet, vol. 344, Issue 8914, Jul. 2, 1994: 23-27.
Hagiwara et al., Autocrine regulation of rat chondrocyte proliferation by natriuretic peptide C and its receptor, natriuretic peptide receptor-B. J Biol Chem. 1994. vol. 269 (No. 14):10729-10733.
Hagiwara et al., cGMP produced in response to ANP and CNP regulates proliferation and differentiation of osteoblastic cells, The American Journal of Physiology, 1996, vol. 270, pp. C1311-C1318.
Harris et al., Developmental and characterization of a conditionally immortalized human fetal osteoblastic cell line. J Bone Miner Res. 1995. vol. 10:178-186.
Herrmann et al., Stimulation of osteoblast activity by homocysteine, J. Cell. Mol. Med., 2008, vol. 12 (No. 4):1205-1210.
International Search Report for PCT/US 11/39277 (filed date of Jun. 6, 2011) dated Oct. 3, 2011, Applicant: University of South Florida et al.
Kalra et al., 2001 The role of C-natriuretic peptide in cardiovascular medicine. Eur Heart J vol. 22:997-1007.
Karsenty & Wagner. Reaching a genetic and molecular understanding of skeletal development. Dev Cell. 2002. vol. 2:389-406.
Lenz et al., Vessel Dilator and C-Type Natriuretic Peptide Enhance the Proliferation of Human Osteoblasts, Pediatric Research, vol. 68, No. 5, 2010, pp. 405-408.

(Continued)

*Primary Examiner* — Xiaozhen Xie
(74) *Attorney, Agent, or Firm* — Nilay J. Choksi; Smith & Hopen, P.A.

(57) ABSTRACT

C-natriuretic peptide (CNP) has been shown to regulate proliferation of mouse and rat osteoblasts. Genetic deletion of CNP results in dwarfism. CNP effects on bone growth involve inhibition of MEK 1 and ERK 1/2 kinases mediated via the intracellular messenger cyclic GMP. Vessel dilator is another natriuretic peptide synthesized by the atrial natriuretic peptide gene whose biologic half-life is 12 times longer than CNP. Vessel dilator's biologic effects on proliferating cells are mediated via inhibiting MEK 1/2 and ERK 1/2 kinases via cyclic GMP. Vessel dilator was not studied previously on osteoblasts. CNP and vessel dilator were tested in dose-response studies enhanced human osteoblasts' proliferation, showing that vessel dilator has identical mechanisms of action to CNP but much longer biologic half-life and effects at lower concentrations. Vessel dilator exhibited therapeutic effect for use in human achondroplasia, short stature and osteoporosis by stimulating osteoblast proliferation.

10 Claims, 2 Drawing Sheets

(56) References Cited

OTHER PUBLICATIONS

Mericq et al., Regulation of fetal rat bone growth by C-type natriuretic peptide and cGMP. Pediat Res. 2000. vol. 47:189-193.
Miyazawa et al., 2002 Cyclic GMP-dependent protein kinase II plays a critical role in C-type natriuretic peptide-mediated endochondral ossification. Endocrinology vol. 143 (Issue 9):3604-3610.
Mori et al., Stimulation of osteoblast proliferation by the cartilage-derived growth promoting factors chondromodulin-I and -II, FEBS Letters, 1997, 406:310-314.
Murakami et al., Constitutive activation of MEK1 in chondrocytes causes Stat1-independent achondroplasia-like dwarfism and rescues the Fgfr3-deficient mouse phenotype. Gene & Dev. 2004. vol. 18:290-305.
Nakao et al., The pharmacokinetics of α-human natriuretic polypeptide in healthy subjects. Eur J Clin Pharmacol. 1986. vol. 31:101-103.
Okazaki, et al., Stimulation of Bone Formation by Recombinant Fibroblast Growth Factor-2 in Callotasis Bone Lengthening of Rabbits, Calcif Tissue Int, 1999, vol. 64:542-546.
Olsen BR et al. Bone development. Annu Rev Cell Dev Biol. 2000. vol. 16:191-220.
Ozasa et al., Complementary antagonistic actions between C-type natriuretic peptide and the MAPK pathway through FGFR-3 in ATDC5 cells. Bone, 2005. vol. 36:1056-1064.
Preliminary Report on Patentability for PCT/US2011/039277 (filed of Jun. 6, 2011) dated Dec. 13, 2012, Applicant: University of South Florida et al.
Pfeifer et al., Intestinal secretory defects and dwarfism in mice lacking cGMP-dependent protein kinase II. Science. 1996. vol. 274:2082-2086.
PVAX™ 200-DEST Vector System, Invitrogen, Biological Defense Systems, accessed at www.invitrogen.com.
Rauch et al., Osteogenesis imperfecta, The Lancet, vol. 363, Apr. 24, 2004, pp. 1377-1385.
Rubin & Rubin, (eds.) Kelly's Textbook of Rheumatology. 8th Edition. Saunders/Elsevier, Philadelphia, PA, USA, pp. 71-91.
Suda et al., C-type natriuretic peptide as an autocrine/paracrine regulator of osteoblasts. Biochem Biophys Res Commun. 1996. vol. 223:1-6.
Sun et al., Vessel dilator and kaliuretic peptide inhibit MEK 1/2 activation in human prostate cancer cells. Anticancer Res. 2007. vol. 27:1387-1392.
Sun et al., Vessel dilator and kaliuretic peptide inhibit ERK 1/2 activation in human prostate cancer cells. Anticancer Res. 2006. vol. 26:3217-3222.
Sun Y. et al. Insulin and epidermal growth factor activation of ERK 1/2 and DNA synthesis is inhibited by four cardiac hormones. J. Cancer Mol. 2007. vol. 3 (No. 4):113-120.
Tamura et al., Critical roles of the guanylyl cyclase B receptor in endochondral ossification and development of female reproductive organs. Proc Natl Acad Sci. 2004. vol. 101 (No. 49):17300-17305.
Teixeira et al., Nitric oxide, C-type natriuretic peptide and cGMP as regulators of endochondral ossification. Dev Biol. 2008. vol. 319:171-178.
Tomasello, Secondary Hyperparathyroidism and Chronic Kidney Disease, Diabetes Spectrum vol. 21, No. 1, 2008, pp. 19-25.
Tsuji & Kunieda, A loss-of-function mutation in natriuretic peptide receptor 2 (Npr2) gene is responsible for disproportionate dwarfism in cn/cn mouse, J Biol Chem. 2005. vol. 280:14288-14292.
Vesely et al., Specific Binding Sites for Prohormone Atrial Natriuretic Peptides 1-30, 31-67 and 99-126, Peptides. vol. 11, pp. 193-197, 1990.
Vesely, Aprotinin blocks the binding of pro atria; natriuretic peptides 1 to 30, 31 to 67, and 99 to 126 to human placental membranes, American Journal of Obstetric & Gynecology, 1991 vol. 165, Issue 3, pp. 567-573.
Vesely, Specific binding site for pro atrial natiuretic factors 1-30, 31-67, and 99-126 on distal nephrons, proximal tubules, renal cortical and medullary membranes, Renal Physiology and Biochemistry, 1992, vol. 15, Issue 1, pp. 23-32.
Vesely. Natriuretic peptides and acute renal failure. Am J Physiol Renal Physiol. 2003. vol. 285:F167-177.
Vesely, Natriuretic Hormones, In: Alpern RJ, Herbert SC (eds) Seldin and Giebisch's the Kidney physiology and pathophysiology, 2013, pp. 1241-1281.
Vesely, Natriuretic Hormones, Seldin and Giebisch's the Kidney physiology and pathophysiology, 2007, pp. 947-977.
Vesely et al.., Three peptides from the atrial natriuretic factor prohormone amino terminus lower blood pressure and produce diuresis, natriuresis, and/or kaliuresis in humans. Circulation Journal of American Heart Association. 1994. vol. 90:1129-1140.
Wang et al., Modulation of lung inflammation by vessel dilator in a mouse model of allergic asthma, Respiratory Research, 2009, 10:66.
Yandle et al., 1986 Metabolic clearance rate and plasma half life of alpha-human atrial natriuretic peptide in man. Life Sci 38:1827-1833.
Yasoda et al., Overexpression of CNP in chondrocytes rescues achondroplasia through a MAPK-dependent pathway. Nat Med. 2004. vol. 10 (No. 1):80-86.
Yasoda et al., Natriuretic peptide regulation of endochondral ossification. Evidence for possible roles of the C-type natriuretic peptide/guanylyl cyclase-B pathway. J Biol Chem. 1998. vol. 273:11695-11700.
Yoder et al., Reduced ability to C-type natriuretic peptide (CNP) to activate natriuretic peptide receptor B (NPR-B) causes dwarfism in 1bab -/- mice. Peptides. 2008. vol. 29:1575-1581.
Zhang et al., Natriuretic peptide receptor A as a novel target for cancer, World Journal of Surgical Oncology, 2014, 12:174.

\* cited by examiner

METHOD OF TREATING SKELETAL DYSPLASIAS USING VESSEL DILATOR

CROSS REFERENCE TO RELATED APPLICATION

This application is a continuation of and claims priority to previously co-pending U.S. Nonprovisional patent application Ser. No. 13/693,372, entitled "Method of Treating Skeletal Dysplasias using Vessel Dilator", filed on Dec. 4, 2012, now abandoned, which is a continuation of and claims priority to International Patent Application Serial No. PCT/US2011/039277, entitled "Method of Treating Skeletal Dysplasias using Vessel Dilator", filed on Jun. 6, 2011, which claims priority to U.S. Provisional Patent Application Ser. No. 61/351,534, entitled "Method of Treating Skeletal Dysplasias using Vessel Dilator", filed on Jun. 4, 2010, all of which are incorporated herein by reference in their entireties.

FIELD OF INVENTION

This invention relates to treatment of skeletal and osteopathic disorders. Specifically, the invention provides for the stimulation of bone growth using vessel dilator.

BACKGROUND OF INVENTION

One in 26,000 births results in achondroplasia, a common cause of dwarfism caused by an autosomal dominant genetic disorder. Bone formation and longitudinal bone growth in long bones, ribs and vertebrae occurs via endochondral ossification in the cartilaginous growth plate, which is located at both ends of the growth plate (Karsenty G, Wagner E F 2002 Reaching a genetic and molecular understanding of skeletal development. Dev Cell 2:389-406; Olsen B R, et al. 2000 Bone development. Annu Rev Cell Dev Biol 16:191-220). One autocrine regulator of bone growth is C-natriuretic peptide (CNP) (Hagiwara H, et al. 1994 Autocrine regulation of rat chondrocyte proliferation by natriuretic peptide C and its receptor, natriuretic peptide receptor-B. J Biol Chem 269:10729-10733; Hagiwara H, et al. 1996 cGMP produced in response to ANP and CNP regulates proliferation and differentiation of osteoblastic cells. Am J Physiol 270:C1311-C1318; Suda M, et al. 1996 C-type natriuretic peptide as an autocrine/paracrine regulator of osteoblasts. Biochem Biophys Res Commun 223:1-6; Yasoda A, et al. 1998 Natriuretic peptide regulation of endochondral ossification. Evidence for possible roles of the C-type natriuretic peptide/guanylyl cyclase-B pathway. J Biol Chem 273:11695-11700; Mericq V, et al. 2000 Regulation of fetal rat bone growth by C-type natriuretic peptide and cGMP. Pediatr Res 47:189-193), a member of the natriuretic peptide hormone family which circulates at a very low level, suggesting that it has very little systemic activity on bone (Kalra P R, et al. 2001 The role of C-natriuretic peptide in cardiovascular medicine. Eur Heart J 22:997-1007; Daggubati S et al. 1997 Adrenomedullin, endothelin, neuropeptide Y, atrial, brain, and C-natriuretic prohormone peptides compared as early heart failure indicators. Cardiovasc Res 36:246-255).

Studies using primary cultures of osteoblast-like cells and chondrocytes have revealed that natriuretic peptides with short half-lives such as CNP and atrial natriuretic peptide (ANP) can regulate proliferation and differentiation of osteoblasts and chondrocytes (Hagiwara H, et al. 1994 Autocrine regulation of rat chondrocyte proliferation by natriuretic peptide C and its receptor, natriuretic peptide receptor-B. J Biol Chem 269:10729-10733; Hagiwara H, et al. 1996 cGMP produced in response to ANP and CNP regulates proliferation and differentiation of osteoblastic cells. Am J Physiol 270:C1311-C1318; Suda M, et al. 1996 C-type natriuretic peptide as an autocrine/paracrine regulator of osteoblasts. Biochem Biophys Res Commun 223:1-6; Yasoda A, et al. 1998 Natriuretic peptide regulation of endochondral ossification. Evidence for possible roles of the C-type natriuretic peptide/guanylyl cyclase-B pathway. J Biol Chem 273:11695-11700; Mericq V, et al. 2000 Regulation of fetal rat bone growth by C-type natriuretic peptide and cGMP. Pediatr Res 47:189-193). CNP stimulates the intracellular messenger cyclic GMP (cGMP) 10-fold more in chondrocytes than ANP (Hagiwara H, et al. 1994 Autocrine regulation of rat chondrocyte proliferation by natriuretic peptide C and its receptor, natriuretic peptide receptor-B. J Biol Chem 269:10729-10733). cGMP itself is important for bone development and plays a role in regulating growth and differentiation of osteoblasts (Hagiwara H, et al. 1996 cGMP produced in response to ANP and CNP regulates proliferation and differentiation of osteoblastic cells. Am J Physiol 270:C1311-C1318; Suda M, et al. 1996 C-type natriuretic peptide as an autocrine/paracrine regulator of osteoblasts. Biochem Biophys Res Commun 223:1-6; Yasoda A, et al. 1998 Natriuretic peptide regulation of endochondral ossification. Evidence for possible roles of the C-type natriuretic peptide/guanylyl cyclase-B pathway. J Biol Chem 273:11695-11700; Mericq V, et al. 2000 Regulation of fetal rat bone growth by C-type natriuretic peptide and cGMP. Pediatr Res 47:189-193, Pfeifer A, et al. 1996 Intestinal secretory defects and dwarfism in mice lacking cGMP-dependent protein kinase II. Science 274:2082-2086; Yasoda A, et al. 2004 Overexpression of CNP in chondrocytes rescues achondroplasia through a MAPK-dependent pathway. Nat Med 10:80-86).

Genetic deletion of CNP or its signaling results in severe skeletal dysplasias caused by reduced chondrocyte proliferation and differentiation (Chusho H, et al. 2001 Dwarfism and early death in mice lacking C-type natriuretic peptide. Proc Natl Acad Sci USA 98:4016-4021; Yoder A R, et al. 2008 Reduced ability to C-type natriuretic peptide (CNP) to activate natriuretic peptide receptor B (NPR-B) causes dwarfism in 1bab −/− mice. Peptides 29:1575-1581). In mice lacking CNP, dwarfism and early death occur (Chusho H, et al. 2001 Dwarfism and early death in mice lacking C-type natriuretic peptide. Proc Natl Acad Sci USA 98:4016-4021). At birth, these mice have a 10% reduction in bone length, but the growth retardation becomes more severe postnatally and 70% of the mice die in the first 100 days after birth (Chusho H, et al. 2001 Dwarfism and early death in mice lacking C-type natriuretic peptide. Proc Natl Acad Sci USA 98:4016-4021). Cartilage-specific overexpression of CNP partially rescues the achondroplasia dwarfism of the CNP-deficient mice, suggesting that CNP stimulates bone growth through direct effects on chondrocytes (Yasoda A, et al. 2004 Overexpression of CNP in chondrocytes rescues achondroplasia through a MAPK-dependent pathway. Nat Med 10:80-86). Contrarily, mice with overexpression of CNP in cartilage have prominent skeletal overgrowth (Yasoda A, et al. 2004 Overexpression of CNP in chondrocytes rescues achondroplasia through a MAPK-dependent pathway. Nat Med 10:80-86). Overexpression of CNP has also been associated with overgrowth and bone abnormalities in a 14-year-old girl (Bocciardi R, et al. 2007 Overexpression of the C-type natriuretic peptide (CNP) is associated with overgrowth and bone anomalies in an individual with balanced t(2;7) translocation. Hum Mutat 28:724-731). Functional inactivation of the natriuretic peptide (NPR)-B receptor that binds CNP (Tamura N, et al. 2004 Critical roles of the guanylyl cyclase B receptor in endochondral ossification and development of female reproductive organs. Proc Natl Acad Sci USA 101:17300-17305; Tsuji T, Kunieda T 2005 A loss-of-function mutation in natriuretic peptide receptor 2 (Npr2) gene is responsible for disproportionate dwarfism in cn/cn mouse. J Biol Chem 280:14288-14292) or gene encoding for cGMP protein kinase II through which cGMP effects are mediated also produces dwarfism (Pfeifer A, et al. 1996 Intestinal secretory defects and dwarfism in mice lacking cGMP-dependent protein kinase II. Science 274: 2082-2086; Miyazawa T, et al. 2002 Cyclic GMP-dependent protein kinase II plays a critical role in C-type natriuretic peptide-mediated endochondral ossification. Endocrinology 143:3604-3610; Teixeira C C, et al. 2008 Nitric oxide, C-type natriuretic peptide and cGMP as regulators of endochondral ossification. Dev Biol 319:171-178).

CNP and ANP are ring-structured natriuretic peptides with very short half-lives of <3 min in the circulation (Kalra P R, et al. 2001 The role of C-natriuretic peptide in cardiovascular medicine. Eur Heart J 22:997-1007, Teixeira C C, et al. 2008 Nitric oxide, C-type natriuretic peptide and cGMP as regulators of endochondral ossification. Dev Biol 319:171-178; Nakao K, et al. 1986 The pharmacokinetics of α-human natriuretic polypeptide in healthy subjects. Eur J Clin Pharmacol 31:101-103; Yandle T G, et al. 1986 Metabolic clearance rate and plasma half life of alpha-human atrial natriuretic peptide in man. Life Sci 38:1827-1833). Their biologic effects last for <30 min. Vessel dilator is a linear natriuretic peptide synthesized by the ANP gene (Brenner B M, et al. 1990 Diverse biological action of atrial natriuretic peptide. Physiol Rev 70:665-699; Vesely D L 2003 Natriuretic peptides and acute renal failure. Am J Physiol Renal Physiol 285:F167-F177; Vesely D L 2007 Natruiretic hormones. In: Alpern R J, Herbert S C (eds.) Seldin and Giebisch's The Kidney: Physiology and Pathophysiology. 4th ed. Elsevier, Inc., Amsterdam, The Netherlands, pp 947-977) that has a circulatory half-life of 107 min (Ackerman B H, et al. 1997 Disposition of vessel dilator and long-acting natriuretic peptide in healthy humans after a one-hour infusion. J Pharmacol Exp Ther 282:603-608) and its biologic effects last >6 h (Vesely D L, et al. 1994 Three peptides from the atrial natriuretic factor prohormone amino terminus lower blood pressure and produce diuresis, natriuresis, and/or kaliuresis in humans. Circulation 90:1129-1140).

The compositions currently used for treatment of skeletal disorders have a short-lived in vivo residence. It would therefore be beneficial to develop longer-lived compounds, facilitating fewer treatments with improved effect.

SUMMARY OF THE INVENTION

Vessel dilator has biologic effects that last 12-times longer than CNP, ANP or BNP as above which makes it unique and preferable for therapy as with its longer half-life it can be given less frequently for treatment. Because vessel dilator is a natriuretic peptide hormones with similar cGMP mechanism of action but much longer biologic effects than CNP or ANP (Kalra P R, et al. 2001 The role of C-natriuretic peptide in cardiovascular medicine. Eur Heart J 22:997-1007; Teixeira C C, et al. 2008 Nitric oxide, C-type natriuretic peptide and cGMP as regulators of endochondral ossification. Dev Biol 319:171-178; Nakao K, et al. 1986 The pharmacokinetics of α-human natriuretic polypeptide in healthy subjects. Eur J Clin Pharmacol 31:101-103; Yandle T G, et al. 1986 Metabolic clearance rate and plasma half-life of alpha-human atrial natriuretic peptide in man. Life Sci 38:1827-1833; Vesely D L, et al. 1994 Three peptides from the atrial natriuretic factor prohormone amino terminus lower blood pressure and produce diuresis, natriuresis, and/or kaliuresis in humans. Circulation 90:1129-1140), it was determined that a natriuretic peptide with at least 12-fold longer biologic effects (Vesely D L, et al. 1994 Three peptides from the atrial natriuretic factor prohormone amino terminus lower blood pressure and produce diuresis, natriuresis, and/or kaliuresis in humans. Circulation 90:1129-1140) increased osteoblasts' proliferation such as CNP. Vessel dilator and CNP were compared directly against each other in dose response curves to determine their comparative ability to enhance osteoblast proliferation.

Surprisingly, it was discovered that the cardiac hormone vessel dilator stimulated the proliferation of osteoblasts, which results in the formation of new bone. Vessel dilator exhibited biologic effects 12 times longer than CNP, ANP, or BNP. As such, vessel dilator was used to treat skeletal disorders in patients. Optionally, vessel dilator is administered at a concentration of between 10 pM and 10 nM, including 1 nM, 100 pM, and 10 pM. Appropriate concentrations of vessel dilator for administration may be calculated in pg and/or ng/kg body weight for infusion by dividing the desired concentration in molarity by vessel dilator's known molecular weight of 3878.31. For example, dividing 100 pM by the molecular weight provides an administration amount of 0.026 pg/kg.

Vessel dilator and C-natriuretic peptide (CNP) were compared directly against each other in dose-response curves to determine their comparative ability to enhance osteoblast proliferation, with vessel dilator exhibiting better results than CNP. Vessel dilator was found to stimulate osteoblasts at 1000-lower concentrations than CNP, and possess biologic effects that last longer than 6 hours compared to less than 30 minutes for CNP, ANP and BNP. This permits vessel dilator to be administered 4 times per day, such as about every 6 hours or at every 6 hours.

The unique findings for cardiac hormone vessel dilator are useful for the treatment of achondroplastic dwarfs and other skeletal dysplasias. Examples of skeletal disorders that are treatable with the present invention include achondroplasia skeletal dysplasias and other dysplasias, short stature, osetopenia, osteoporosis, osteomalacia, hypoparathyroidism, tumor associated osteomalacia, rickets, osteogenesis imperfecta, osteitis fibrosa cystic secondary to hyperparathyroidism, Paget's disease, and osteitis deformans, short stature, and osteoporosis. For example, osteoporosis is a common disease in adults with current treatments such as bisphosphonates, parathyroid hormone, calcitonin and 1,25-dihydroxy vitamin D all working via inhibiting osteoclasts. Current treatment for osteoporosis inhibits the activity of osteoclasts, preventing break-down of old bone. Conversely, the invention stimulates osteoblasts to form new bone. There is no information on this novel use of vessel dilator stimulating osteoblasts. Stimulating osteoblasts to form new healthy bone is a beneficial advance in the treatment of osteoporosis.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
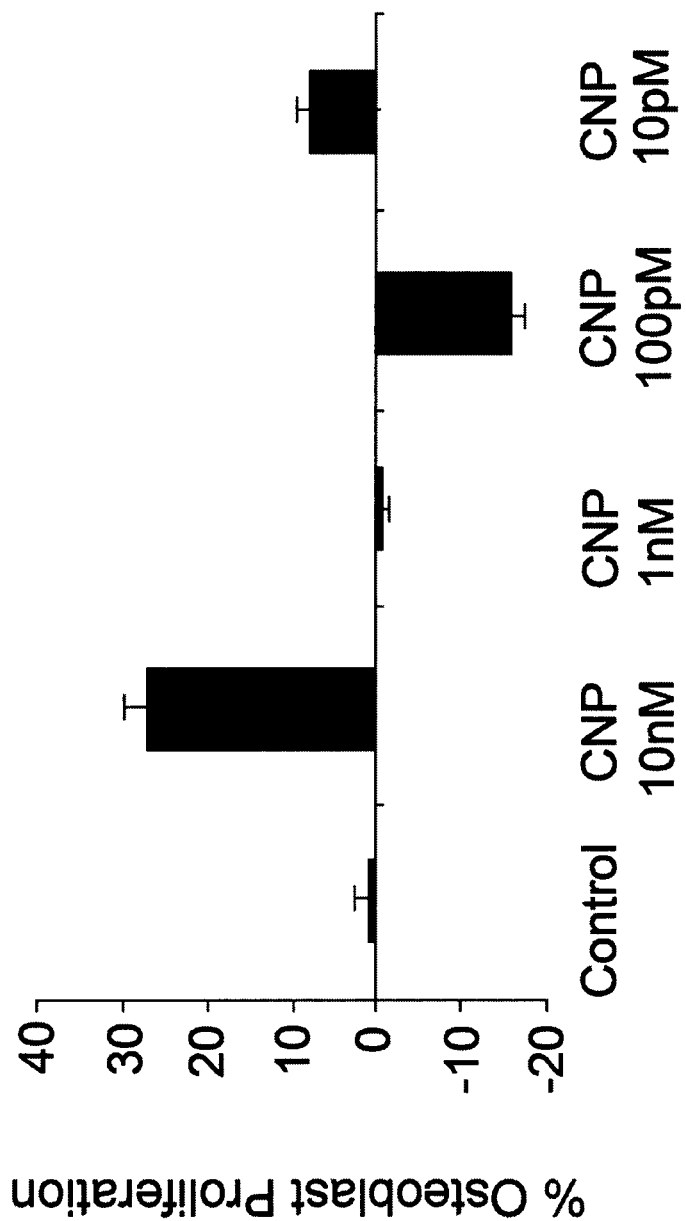
FIG. 1 is a graph showing C-natriuretic peptide (CNP) enhances human osteoblast proliferation at its 10 nM concentration by 27% (p=0.02) when evaluated by the Mann-Whitley (Wilcoxon rank-sum test). CNP did not significantly enhance human osteoblast proliferation at its 1 nM, 100 pM, and 10 pM concentrations when evaluated by Mann-Whitley test.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

As used herein, "about" means approximately or nearly and in the context of a numerical value or range set forth means±15% of the numerical.

As used herein, "atrial natriuretic peptide" (ANP), also known as atrial natriuretic factor (ANF), atrial natriuretic hormone (ANH), or atriopeptin, is a vasodilator, and hormone encoded by C-terminal residues 99-126 of the natriuretic peptide precursor C gene (NPPC; GenBank Accession Number NM_024409.1). ANP is a 28-amino acid peptide with a 17-amino acid ring in the middle of the molecule. It is secreted by heart muscle cells to reduce blood pressure by lowering water, sodium and adipose loads on the circulatory system.

As used herein, "C-type natriuretic peptide" (CNP) is a 22 amino acid peptide having a 17-amino acid ring, as described by Brevic (U.S. application Ser. No. 12/677,304, filed Sep. 9, 2008), and is generated from the natriuretic peptide precursor C gene (NPPC; GenBank Accession Number NM_024409.1).

As used herein, "extracellular signal-regulated kinase 1/2" (ERK 1/2) are 44-kDa(ERK1) and 42-kDa (ERK2) serine-threonine protein kinases that regulate cardiac hypertrophy and myocyte survival, cell proliferation, and cell differentiation.

As used herein, "mitogen-activated protein kinase" (MAP kinase 1/2, MEK1/2) are dual specificity kinases that activate MAPKs (ERK-1/2) having a size of about 45 kDa (MEK 1) and 44 kDa (MEK 2). MEK 1/2 are highly specific, phosphorylating and activating the 44 kDa and 42 kDa MAP kinases, and responsible for promoting cell cycle progression. MEK 1/2 also play an important role in modulating the survival of hematopoietic cells, and the differentiation of certain cell types, such as neuronal cells, maturation of thymocytes from $CD4^-CD8^-$ to $CD4^+CD8^+$ cells, and development of the visual cortex.

As used herein, "mitogen-activated protein kinase" (MAPK), is a serine/threonine-specific protein kinase that responds to extracellular stimuli to regulate various cellular activities, such as gene expression, mitosis, differentiation, proliferation, and cell survival/apoptosis.

The term "patient" is used herein to describe an animal, preferably a human, to whom treatment, including prophylactic treatment, with the compounds according to the present invention, is provided. For treatment of the conditions or disease states which are specific for a specific animal such as a human patient, the term patient refers to that specific animal.

The term "effective amount" is used herein to describe concentrations or amounts of compounds, such as vessel dilator, that are effective for producing an intended result including regulating growth and differentiation of osteoblasts, to address skeletal disorders or other pathologic conditions including achondroplasia skeletal dysplasias and other dysplasias, short stature, osetopenia, osteoporosis, osteomalacia, hypoparathyroidism, tumor associated osteomalacia, rickets, osteogenesis imperfecta, osteitis fibrosa cystic secondary to hyperparathyroidism, Paget's Disease, and osteitis deformans. Compositions according to the present invention may be used to effect proliferation and differentiation of osteoblastic cells to produce a favorable change in the bone or skeletal tissue, or in the disease or condition treated, whether that change is an improvement such as stopping or reversing the degeneration of a disease or condition, reducing a bone density deficit, or a complete cure of the disease or condition treated.

The term "administration" or "administering" is used throughout the specification to describe the process by which compounds of the subject invention, such as vessel dilator, are delivered to a patient for therapeutic purposes. Compounds of the subject invention can be administered a number of ways including, but not limited to, parenteral (such term referring to intravenous and intra-arterial as well as other appropriate parenteral routes), subcutaneous, intraperitoneal, intraventricular, among others which term allows compounds of the subject invention to diffuse to the ultimate target site where needed. The compounds can be administered systemically or to a target anatomical site, permitting the compounds to contact target cells, causing the target cells to proliferate and/or differentiate in response to the compounds (e.g., site-specific differentiation).

Administration will often depend upon the disease or condition treated and may preferably be via a parenteral route, for example, intravenously, or by direct administration into the affected bone. For example, vessel dilator may be administered via direct injection into the bone, or may be administered systemically. In a preferred embodiment of the present invention, the route of administration for treating an individual is systemic, via intravenous, intra-arterial administration, subcutaneous, or intraperitoneal administration.

The pharmaceutical compositions may further comprise a pharmaceutically acceptable carrier. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject compounds include, but are not limited to, water, saline, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. For example, vessel dilator can be diluted to give a concentration in either 0.9% saline (ie normal saline) or D5W (dextrose 5% in water) for infusion.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

In Vitro Testing of Vessel Dilator.

A cell line (ATCC number CRL-11372) of human osteoblast cells was purchased from the American Type Culture Association (ATCC, Manassas, Va.). Propagation of the human osteoblast cells was in a 1:1 mixture of Ham's F12 Medium and Dulbecco's Modified Eagles Medium (DMEM) with 2.5 mM L-glutamine without phenol red. Base medium was supplemented with 0.3 mg/mL of Geneticin (G418) antibiotic and 10% fetal bovine serum (Harris S A, et al. 1995 Developmental and characterization of a conditionally immortalized human fetal osteoblastic cell line. J Bone Miner Res 10:178-186). Cells were incubated at a temperature of 34° C. in 5% $CO_2$ at which they have rapid cell division, doubling every 36 hours (Harris S A, et al. 1995 Developmental and characterization of a conditionally immortalized human fetal osteoblastic cell line. J Bone Miner Res 10:178-186). Immunostaining of these post-confluent differentiated human osteoblasts showed that high levels of osteopontin, osteonectin, bone sialoprotein and type 1 collagen were expressed (Harris S A, et al. 1995 Developmental and characterization of a conditionally immortalized human fetal osteoblastic cell line. J Bone Miner Res 10:178-186). Cells were dispensed into new flasks with subculturing every 6-8 days. The medium was changed every 3 days.

After the osteoblast cells were subcultured for 24 h, ~5000 cells in 200 μL of the above media were then seeded (day 1) into 96-well plates (Nuclon, Roskilde, Denmark). After overnight incubation at 34° C. in 5% $CO_2$, the media was removed (day 2), and 50 μL of fresh media was added to control wells, blank wells (with no cells inside), and 50 μL of media with 10 picomolar (pM), 100 pM, 1 nanomolar (nM), or 10 nM of CNP or vessel dilator. At day 5, in these experiments, 50 μL of fresh media was added to the controls, blank wells, and 50 μL of media with 1 nM, 10 nM, 10 pM, and 100 pM of the respective natriuretic hormones for a total volume of 100 μL of media in each well. At day 7, 20 μL of Cell Titer 96® Aqueous One Solution (Promega Corporation, Madison, Wis.) was added to each well containing 1004 of medium and allowed to incubate for 4 h in 5% $CO_2$ atmosphere before recording absorbance at 490 nm with a 96-well plate reader (Cory A H, et al. 1991 Use of aqueous soluble tetrazolium/formazan assay for growth assays in culture. Cancer Commun 3:207-212). There were 15 observations of vessel dilator at each concentration and 16 observations of CNP at each concentration. The peptide hormones used in this investigation were from Phoenix Pharmaceuticals, Inc., Burlingame, Calif.

Cell Proliferation.

Cell proliferation of human osteoblasts was examined with the Cell Titer 96 Aqueous One Solution cell proliferation assay (Promega Corp.). This colorimetric method determines the viable cells' proliferation by recording the absorption at 490 nm with a 96-well plate reader (Cory A H, et al. 1991 Use of aqueous soluble tetrazolium/formazan assay for growth assays in culture. Cancer Commun 3:207-212) after incubating the respective cells at 37° C. for 4 h in a 5% $CO_2$ atmosphere.

Approximately 5000 human osteoblast cells were in each well. The proliferation assay detects the number of viable cells in proliferation using a tetrazolium compound (3-[4,5-dimethylthiazol-2-yl]-5-[3-carboxymethoxyphenyl]-2-[4-sulfophenyl]-2H-tetrazolium, inner salt; MTS) and an electron coupling reagent [phenazine ethosulfate (PES)]. PES has enhanced chemical stability, which allows it to be combined with MTS to form a stable solution (Cory A H, et al. 1991 Use of aqueous soluble tetrazolium/formazan assay for growth assays in culture. Cancer Commun 3:207-212). The MTS tetrazolium compound (Owen's reagent) is bioreduced by living cells into a colored formazan product that is measurable at 490 nM in a spectrophotometer, thereby eliminating any nonviable (i.e. dead) cells that would not be proliferating (Cory A H, et al. 1991 Use of aqueous soluble tetrazolium/formazan assay for growth assays in culture. Cancer Commun 3:207-212). This method measure only viable cells' proliferation as dead cells are unable to reduce the MTS tetrazolium compound to a colored formazan product.

All data are expressed as mean±SEM. Statistical significance was determined by the Mann-Whitney test (also called Wilcoxon rank-sum test) for different sample sizes. For the CNP group, there were 16 data points for each concentration and eight controls. For the vessel dilator group, there were 15 data points for each concentration and 24 controls.

CNP at its 10 nM concentration enhanced human osteoblast proliferation 27% (n=16) compared with controls, seen in FIG. 1 (n=8; p=0.02). There was no significant enhancement of osteoblast proliferation at CNP concentrations of 1 nM, 100 pM, and 10 pM, seen in FIG. 1. Thus, at 1 nM, there was a minus 1% enhancement, and at 100 pM, there was a minus 16% enhancement of osteoblast proliferation with CNP, seen in FIG. 1.

Figure 2:
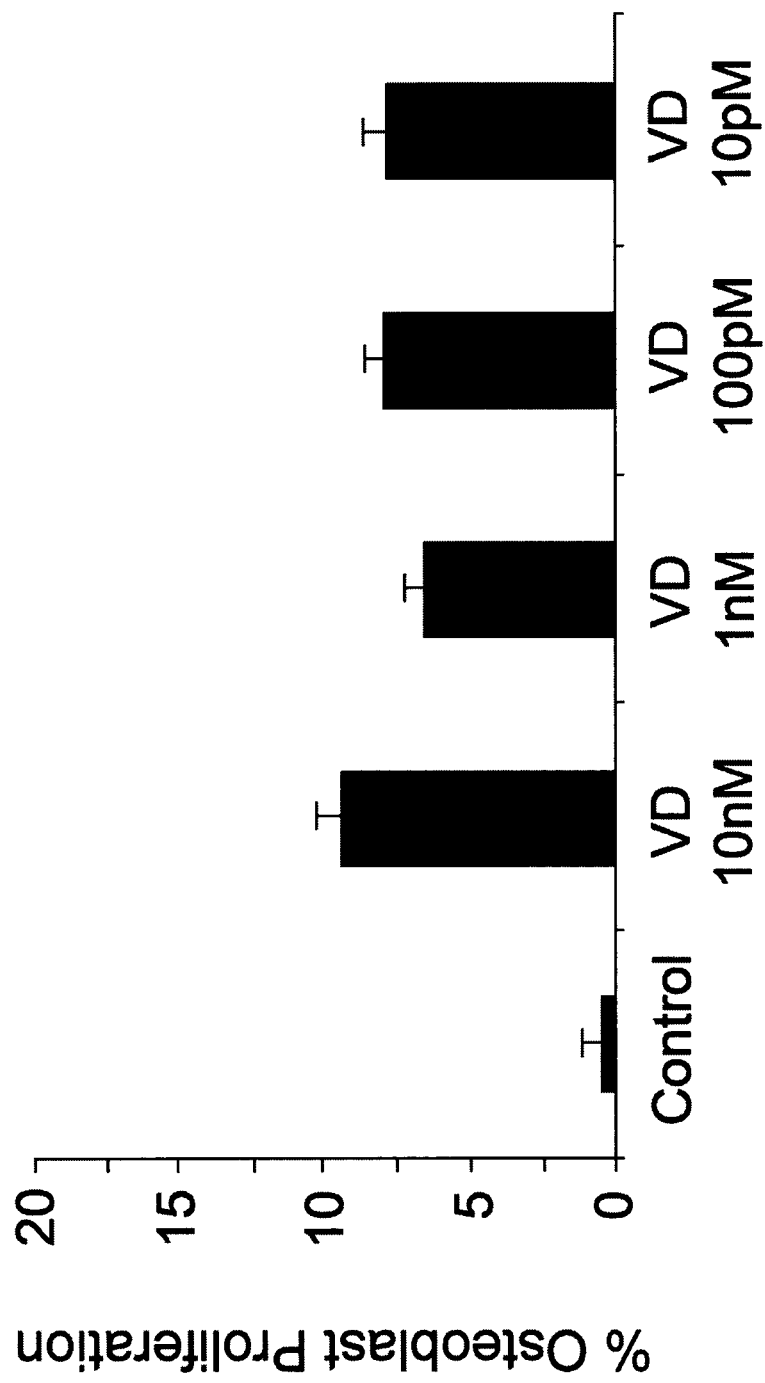
FIG. 2 is a graph showing vessel dilator enhanced the proliferation of human osteoblasts over a concentration of range of 10 nM to 10 pM (p<0.01 or less) when evaluated by Mann-Whitley test. The 100 pM and 10 pM concentrations in this graph are in the circulating physiologic range of vessel dilator (Daggubati, et al., 1997 Adrenomedullin, endothelin, neuropeptide Y, atrial, brain, and C-natriuretic prohormone peptides compared as early heart failure indicators. Cardiovascular Res. 36:246-255).

Vessel dilator at its 10 nM concentration (n=15) enhanced the proliferation of human osteoblasts 8% compared with controls, seen in FIG. 2 (n=24; p=0.0018). Decreasing the concentration of vessel dilator 10-fold to 1 nM resulted in a 6% enhancement of the proliferation of human osteoblasts (p<0.01). With a 100-fold decrease in the concentration of vessel dilator to 100 pM, there was still a 7% enhancement of the proliferation of human osteoblasts, as seen in FIG. 2 (p=0.0073). Vessel dilator at 10 pM stimulated human osteoblast proliferation 8% (p=0.01).

Comparing the effects of CNP and vessel dilator on human osteoblast proliferation, as seen in FIG. 1 versus FIG. 2, revealed that CNP-stimulated osteoblast proliferation to a greater extent at its 10 nM concentration versus 10 nM concentration of vessel dilator (p=0.048). However, at their respective 1 nM and 100 pM concentrations vessel dilator caused a more significant (p<0.05) enhancement of human osteoblast proliferation.

CNP is expressed in fetal bones and accelerates longitudinal growth of fetal rat metatarsal bones in organ culture (Mericq V, et al. 2000 Regulation of fetal rat bone growth by C-type natriuretic peptide and cGMP. Pediatr Res 47:189-193). CNP in the present investigation was found to stimulate human osteoblast proliferation for the first time, extending previous findings that CNP can enhance osteoblast proliferation in rat (Hagiwara H, et al. 1996 cGMP produced in response to ANP and CNP regulates proliferation and differentiation of osteoblastic cells. Am J Physiol 270: C1311-C1318) and mouse (Suda M, et al. 1996 C-type natriuretic peptide as an autocrine/paracrine regulator of osteoblasts. Biochem Biophys Res Commun 223:1-6) osteoblasts. CNP dose-response studies on human osteoblasts revealed that at 10 pM, which is CNP's physiological circulating concentration (Daggubati S, et al. 1997 Adrenomedullin, endothelin, neuropeptide Y, atrial, brain, and C-natriuretic prohormone peptides compared as early heart failure indicators. Cardiovasc Res 36:246-255), CNP could not enhance human osteoblast proliferation suggesting that CNP may not be a systemic physiologic regulator of osteoblast function. This would confirm previous studies of CNP on osteoblast function of mice osteoblasts (Suda M, et al. 1996 C-type natriuretic peptide as an autocrine/paracrine regulator of osteoblasts. Biochem Biophys Res Commun 223:1-6), rat osteoblasts (Hagiwara H, e al. 1996 cGMP produced in response to ANP and CNP regulates proliferation and differentiation of osteoblastic cells. Am J Physiol 270:C1311-C1318), and rat chondrocytes (Hagiwara H, et al. S 1994 Autocrine regulation of rat chondrocyte proliferation by natriuretic peptide C and its receptor, natriuretic peptide receptor-B. J Biol Chem 269:10729-10733; Mericq V, et al. 2000 Regulation of fetal rat bone growth by C-type natriuretic peptide and cGMP. Pediatr Res 47:189-193) where CNP did not have any effects on osteoblasts in the pM range. However, the importance of CNP in bone growth is illustrated by genetic deletion of CNP resulting in skeletal dysplasia (Chusho H, et al. 2001 Dwarfism and early death in mice lacking C-type natriuretic peptide. Proc Natl Acad Sci USA 98:4016-4021; Yoder A R, Kruse A C, Earhart C A, Ohlendorf D H, Potter L R 2008 Reduced ability to C-type natriuretic peptide (CNP) to activate natriuretic peptide receptor B (NPR-B) causes dwarfism in 1bab −/− mice. Peptides 29:1575-1581) with mice lacking CNP having dwarfism (Chusho H, et al. 2001 Dwarfism and early death in mice lacking C-type natriuretic peptide. Proc Natl Acad Sci USA 98:4016-4021). Further evidence of CNP importance for bone growth is that mice overexpressing CNP in cartilage have skeletal overgrowth (Yasoda A, et al. 2004 Overexpression of CNP in chondrocytes rescues achondroplasia through a MAPK-dependent pathway. Nat Med 10:80-86), and a 14-y-old girl with overexpression of CNP, with a doubling of CNP in plasma, had bone overgrowth and who was >97 percentile in length at birth and had arachnodactyly of hands and feet with a very long hallux bilaterally at 14 years old (Bocciardi Re al. 2007 Overexpression of the C-type natriuretic peptide (CNP) is associated with overgrowth and bone anomalies in an individual with balanced t(2;7) translocation. Hum Mutat 28:724-731). These studies would suggest that because CNP does not stimulate human, rat, or mouse osteoblasts at its circulating physiologic concentrations, its effects on bone are via an autocrine/paracrine process.

The gene for CNP is expressed in bone (Mericq V, et al. 2000 Regulation of fetal rat bone growth by C-type natriuretic peptide and cGMP. Pediatr Res 47:189-193) to allow it to be an autocrine/paracrine regulator of bone. This is the first investigation demonstrating that vessel dilator, a linear structured peptide hormone as opposed to a ring-structured CNP (Brenner B M, et al. 1990 Diverse biological action of atrial natriuretic peptide. Physiol Rev 70:665-699; Vesely D L 2003 Natriuretic peptides and acute renal failure. Am J Physiol Renal Physiol 285:F167-F177; Vesely D L 2007 Natruiretic hormones. In: Alpern R J, Herbert S C (eds) Seldin and Giebisch's The Kidney: Physiology and Pathophysiology. 4th ed. Elsevier, Inc., Amsterdam, The Netherlands, pp 947-977), can stimulate osteoblast proliferation. That vessel dilator can enhance human osteoblast proliferation is important because its circulating half-life is 36-fold longer than CNP, at 107 min for vessel dilator versus <3 min for CNP; (Kalra P R, et al. 2001 The role of C-natriuretic peptide in cardiovascular medicine. Eur Heart J 22:997-1007; Teixeira C C, et al. 2008 Nitric oxide, C-type natriuretic peptide and cGMP as regulators of endochondral ossification. Dev Biol 319:171-178; Nakao K, et al. 1986 The pharmacokinetics of α-human natriuretic polypeptide in healthy subjects. Eur J Clin Pharmacol 31:101-103; Yandle T G, et al. 1986 Metabolic clearance rate and plasma half life of alpha-human atrial natriuretic peptide in man. Life Sci 38:1827-1833; Ackerman B H, et al. 1997 Disposition of vessel dilator and long-acting natriuretic peptide in healthy humans after a one-hour infusion. J Pharmacol Exp Ther 282:603-608); and its biologic effects last for >6 h compared with <30 min for ring-structured natriuretic peptides such as CNP and ANP (Vesely D L, et al. 1994 Three peptides from the atrial natriuretic factor prohormone amino terminus lower blood pressure and produce diuresis, natriuresis, and/ or kaliuresis in humans. Circulation 90:1129-1140), which also has enhancing effects in bone growth (Hagiwara H, et al. 1996 cGMP produced in response to ANP and CNP regulates proliferation and differentiation of osteoblastic cells. Am J Physiol 270:C1311-C1318). Vessel dilator, but not CNP, was found to enhance human osteoblast proliferation at its physiologic concentrations in the circulation (Vesely D L, e al. 1994 Three peptides from the atrial natriuretic factor prohormone amino terminus lower blood pressure and produce diuresis, natriuresis, and/or kaliuresis in humans. Circulation 90:1129-1140), further suggesting that vessel dilator may be important for physiologic regulation of bone growth by stimulating osteoblasts. Increasing the concentration of vessel dilator above the physiologic range to pharmacological concentrations did not cause a further increase in its ability to enhance osteoblast proliferation. This information would suggest that bone proteases may be proteolytically degrading this peptide hormone at its higher concentrations. With more vessel dilator present in bone, the bone proteases may become more active in a negative feedback manner, cleaving this peptide hormone resulting in loss of any enhanced biologic activity beyond that observed with physiologic concentrations of vessel dilator.

With respect to the mechanisms of vessel dilator and CNP's enhancement of osteoblast proliferation, cGMP would seem to be an important mediator of their effects because CNP can increase this intracellular mediator in chondrocytes (Hagiwara H, et al. 1994 Autocrine regulation of rat chondrocyte proliferation by natriuretic peptide C and its receptor, natriuretic peptide receptor-B. J Biol Chem 269:10729-10733) and the majority of vessel dilator's effects are mediated via cGMP (Brenner B M, et al. 1990 Diverse biological action of atrial natriuretic peptide. Physiol Rev 70:665-699; Vesely D L 2003 Natriuretic peptides and acute renal failure. Am J Physiol Renal Physiol 285:F167-F177; Vesely D L 2007 Natruiretic hormones. In: Alpern R J, Herbert S C (eds) Seldin and Giebisch's The Kidney: Physiology and Pathophysiology. 4th ed. Elsevier, Inc., Amsterdam, The Netherlands, pp 947-977; Sun Y, et al. 2007 Vessel dilator and kaliuretic peptide inhibit MEK 1/2 activation in human prostate cancer cells. Anticancer Res 27:1387-1392). cGMP itself is important for bone development, which have been shown to regulate proliferation and differentiation of osteoblasts and chondrocytes (Hagiwara H, et al. 1996 cGMP produced in response to ANP and CNP regulates proliferation and differentiation of osteoblastic cells. Am J Physiol 270:C1311-C1318; Suda M, et al. 1996 C-type natriuretic peptide as an autocrine/paracrine regulator of osteoblasts. Biochem Biophys Res Commun 223:1-6; Yasoda A, et al. 1998 Natriuretic peptide regulation of endochondral ossification. Evidence for possible roles of the C-type natriuretic peptide/guanylyl cyclase-B pathway. J Biol Chem 273:11695-11700; Mericq V, et al. 2000 Regulation of fetal rat bone growth by C-type natriuretic peptide and cGMP. Pediatr Res 47:189-193; Pfeifer A, et al. 1996 Intestinal secretory defects and dwarfism in mice lacking cGMP-dependent protein kinase II. Science 274:2082-2086; Yasoda A, et al. 2004 Overexpression of CNP in chondrocytes rescues achondroplasia through a MAPK-dependent pathway. Nat Med 10:80-86).

Inactivation of the gene encoding for cGMP protein kinase II, through which cGMP effects are mediated in bone, also produces achondroplastic dwarfism (Pfeifer A, et al. 1996 Intestinal secretory defects and dwarfism in mice lacking cGMP-dependent protein kinase II. Science 274: 2082-2086; Miyazawa T, et al. 2002 Cyclic GMP-dependent protein kinase II plays a critical role in C-type natriuretic peptide-mediated endochondral ossification. Endocrinology 143:3604-3610; Teixeira C C, et al. 2008 Nitric oxide, C-type natriuretic peptide and cGMP as regulators of endochondral ossification. Dev Biol 319:171-178). Overexpression of CNP in chondrocytes rescues achondroplasia through inhibition of MEK 1 kinase in the mitogen-activated protein kinase (MAPK) pathway (Yasoda A, et al. 2004 Overexpression of CNP in chondrocytes rescues achondroplasia through a MAPK-dependent pathway. Nat Med 10:80-86). Constitutive activation of MEK 1 kinase in chondrocytes causes achondroplasia-like dwarfism in mice (Murakami S, et al. 2004 Constitutive activation of MEK1 in chondrocytes causes Stat1-independent achondroplasia-like dwarfism and rescues the Fgfr3-deficient mouse phenotype. Genes Dev 18:290-305). Vessel dilator inhibits the activation, i.e. phosphorylation of MEK 1/2 kinases by 98% in proliferating prostate cancer cells (Sun Y, et al. 2007 Vessel dilator and kaliuretic peptide inhibit MEK 1/2 activation in human prostate cancer cells. Anticancer Res 27:1387-1392). Vessel dilator appears to inhibit MEK 1/2 kinases in proliferating cells through cGMP. For example, contacting cells with a cGMP antibody blocks vessel dilator effects on MEK 1/2 kinases. Further, cGMP itself can inhibit MEK 1/2 kinases in proliferating cells (Sun Y, et al. 2007 Vessel dilator and kaliuretic peptide inhibit MEK 1/2 activation in human prostate cancer cells. Anticancer Res 27:1387-1392). CNP and 8-bromo cGMP also inhibit mitogen- (fibroblast growth factor) stimulated ERK 1/2 kinases' phosphorylation in ATDC5 cells, a mouse chondrogenic cell line (Ozasa A, et al. 2005 Complementary antagonistic actions between C-type natriuretic peptide and the MAPK pathway through FGFR-3 in ATDC5 cells. Bone 36:1056-1064). Vessel dilator inhibits 96% of the phosphorylation of basal activity of ERK 1/2 kinases in proliferating cells (Sun Y, et al. 2006 Vessel dilator and kaliuretic peptide inhibit activation of ERK 1/2 in human prostate cancer cells. Anticancer Res 26:3217-3222) and completely blocks mitogen; epidermal growth factor, (EGF); and stimulation of ERK 1/2 kinases (Sun Y, et al. 2007 Insulin and epidermal growth factor activation of ERK 1/2 and DNA synthesis is inhibited by four cardiac hormones. J. Cancer Mol 3:113-120). Thus, both vessel dilator and CNP seem to have identical molecular mechanisms of action of stimulating osteoblasts and bone growth via inhibiting MAP kinases MEK 1/2 and ERK 1/2, mediated at least in part by cGMP (Yasoda A, et al. 2004 Overexpression of CNP in chondrocytes rescues achondroplasia through a MAPK-dependent pathway. Nat Med 10:80-86, 29-32; Murakami, et al., 2004 Constitutive activation of MEK1 in chondrocytes causes Stat1-independent achondroplasia-like dwarfism and rescues the Fgfr3-deficient mouse phenotype. Gene & Dev 18:290-305; Ozasa, et al., 2005 Complementary antagonistic actions between C-type natriuretic peptide and the MAPK pathway through FGFR-3 in ATDC5 cells. Bone 36:1056-1064; Sun, et al., 2006 Vessel dilator and kaliuretic peptide inhibit activation of ERK 1/2 in human prostate cancer cells. Anticancer Res. 26:3217-3222; Sun, et al., 2007 Insulin and epidermal growth factor activation of ERK 1/2 and DNA synthesis is inhibited by four cardiac hormones. J. Cancer Mol. 3:113-120).

With respect to potential treatment of bone diseases, CNP has been suggested to be a new treatment strategy for achondroplasia (Ozasa A, et al. 2005 Complementary antagonistic actions between C-type natriuretic peptide and the MAPK pathway through FGFR-3 in ATDC5 cells. Bone 36:1056-1064). Vessel dilator, with its 36-fold longer half-life and significantly longer biologic effects than CNP, i.e. >12 times longer (Vesely D L, et al. 1994 Three peptides from the atrial natriuretic factor prohormone amino terminus lower blood pressure and produce diuresis, natriuresis, and/or kaliuresis in humans. Circulation 90:1129-1140), would seem to be a better choice for treatment of bone disease such as dwarfism because it can be given less frequently with similar therapeutic results. Furthermore, vessel dilator stimulates osteoblastic proliferation over a concentration range of 10 nM through 10 pM, whereas CNP at concentration <10 nM did not significantly enhance human osteoblast proliferation. CNP's half-life is very short, at about 3 min, in vivo whereas vessel dilator's half-life of >6 h (Vesely D L, et al. 1994 Three peptides from the atrial natriuretic factor prohormone amino terminus lower blood pressure and produce diuresis, natriuresis, and/or kaliuresis in humans. Circulation 90:1129-1140) would suggest it could be given four times per day to affect bone growth. As vessel dilator can be given on a reasonable schedule of four times per day, it may have a role in the treatment of short stature in children by enhancing their osteoblast proliferation, indicating that vessel dilator can be utilized in lower concentrations to obtain the same effects as CNP on bone.

In addition to growth disorders in children, CNP and vessel dilator may have a therapeutic role in treating a common bone disease in adults, i.e. osteoporosis. Current therapeutic agents for osteoporosis concentrate on inhibiting osteoclasts (Rubin J E, Rubin C T 2009 Biology, physiology, and morphology of bone. In: Firestein G S, et al. (eds) Kelly's Textbook of Rheumatology. 8th ed. Elsevier, Philadelphia, Pa., pp 71-91). Bisphosphonates such as alendronate, parathyroid hormone (PTH), calcitonin, and 1,25-dihydroxy vitamin D, all work via inhibiting osteoclasts (Rubin J E, Rubin C T 2009 Biology, physiology, and morphology of bone. In: Firestein G S, et al. (eds) Kelly's Textbook of Rheumatology. 8th ed. Elsevier, Philadelphia, Pa., pp 71-91). Sex steroids such as estrogens and testosterone do stimulate osteoblasts (Rubin J E, Rubin C T 2009 Biology, physiology, and morphology of bone. In: Firestein G S, et al. (eds) Kelly's Textbook of Rheumatology. 8th ed. Elsevier, Philadelphia, Pa., pp 71-91) but are usually given only in cases of documented low testosterone and/or estrogens because of their side effects. Estrogens, for example, are not currently given for osteoporosis even when the person is post-menopausal with low estrogen levels by some physicians because of their potential cardiovascular risk (Rubin J E, Rubin C T 2009 Biology, physiology, and morphology of bone. In: Firestein G S, et al. (eds) Kelly's Textbook of Rheumatology. 8th ed. Elsevier, Philadelphia, Pa., pp 71-91). Sodium fluoride stimulates osteoblasts and has been used for vertebral fractures but even though bone mass increased secondary to sodium fluoride, it does not decrease the incidence of fractures. An agent that stimulates osteoblasts without the side effects of sodium fluoride or sex steroids and that will cause bone formation via osteoblasts rather than inhibiting old bone in place (via osteoclasts) has been sought for decades. As seen herein, vessel dilator was demonstrated to stimulate human osteoblasts, suggesting that it may provide a new therapeutic option for bone disease. Vessel dilator would be a preferred option over CNP because of its much longer biologic activity for >6 h compared with <30 min for CNP (Vesely D L, et al. 1994 Three peptides from the atrial natriuretic factor prohormone amino terminus lower blood pressure and produce diuresis, natriuresis, and/or kaliuresis in humans. Circulation 90:1129-1140), and that treatment every 30 min with CNP would be very impractical.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treatment of skeletal and osteopathic disorders using vessel dilator, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating a skeletal disorder, comprising administering a therapeutically effective amount of vessel dilator to a patient having the skeletal disorder,
   wherein the skeletal disorder is achondroplasia skeletal dysplasia, osteopenia, osteoporosis, osteogenesis imperfecta, or osteitis fibrosa cystica secondary to hyperparathyroidism;
   wherein the vessel dilator is administered at a concentration of between 10 pM and 10 nM or at a dosage of between 0.000258 ng/kg and 0.0028 pg/kg of body weight of the patient; and
   wherein administration of the vessel dilator stimulates osteoblast proliferation in the patient.

2. The method of claim 1, wherein the skeletal disorder is osteoporosis.

3. The method of claim 1, wherein the vessel dilator is administered at a concentration of between 10 pM and 10 nM.

4. The method of claim 3, wherein the vessel dilator is administered at a concentration of between 10 pM and 100 pM.

5. The method of claim 3, wherein the vessel dilator is administered at a concentration of 1 nM.

6. The method of claim 3, wherein the vessel dilator is administered at a concentration of 100 pM.

7. The method of claim 3, wherein the vessel dilator is administered at a concentration of 10 pM.

8. The method of claim 1, wherein the vessel dilator is administered at a dosage of between 0.000258 ng/kg and 0.0028 pg/kg of body weight of the patient.

9. The method of claim 1, wherein the vessel dilator has a half-life of 107 minutes.

10. A method of treating achondroplasia skeletal dysplasia, comprising administering a therapeutically effective amount of vessel dilator to a patient having achondroplasia skeletal dysplasia,
    wherein the vessel dilator is administered at a concentration of 10 pM and at a dosage of 0.0028 pg/kg of body weight of the patient;
    wherein the vessel dilator is administered four (4) times a day at every six (6) hours;
    wherein the vessel dilator has a half-life of 107 minutes; and
    wherein administration of the vessel dilator stimulates osteoblast proliferation in the patient.

* * * * *